United States Patent
Sagawa et al.

(10) Patent No.: US 9,399,030 B2
(45) Date of Patent: Jul. 26, 2016

(54) TOPICALLY APPLIED CIRCULATION ENHANCING AGENT AND SKIN AND HAIR COSMETIC AND BATH AGENT CONTAINING THE SAME

(75) Inventors: Koichiro Sagawa, Kanagawa (JP); Yoshinobu Takino, Kanagawa (JP); Yusuke Amino, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 2959 days.

(21) Appl. No.: 11/283,931

(22) Filed: Nov. 22, 2005

(65) Prior Publication Data

US 2006/0287390 A1 Dec. 21, 2006

Related U.S. Application Data

(60) Provisional application No. 60/675,895, filed on Apr. 29, 2005.

(30) Foreign Application Priority Data

Feb. 1, 2005 (JP) .................. 2005-025219

(51) Int. Cl.
*A61K 31/22* (2006.01)
*A61K 31/23* (2006.01)

(52) U.S. Cl.
CPC ............... *A61K 31/22* (2013.01); *A61K 31/23* (2013.01)

(58) Field of Classification Search
None
See application file for complete search history.

(56) References Cited

U.S. PATENT DOCUMENTS

| | | | | |
|---|---|---|---|---|
| 6,333,241 B1 * | 12/2001 | Kim | ............... | 438/398 |
| 6,333,421 B1 | 12/2001 | Yazawa et al. | | |
| 6,579,543 B1 * | 6/2003 | McClung | ............... | 424/728 |
| 7,414,075 B2 * | 8/2008 | Tani et al. | ............... | 514/546 |
| 2001/0011083 A1 * | 8/2001 | Barr et al. | ............... | 514/159 |
| 2003/0013753 A1 * | 1/2003 | Aung-Din | ............... | 514/419 |
| 2003/0105159 A1 * | 6/2003 | McCleary et al. | ............... | 514/460 |
| 2005/0239883 A1 * | 10/2005 | Tani et al. | ............... | 514/546 |
| 2005/0271606 A1 | 12/2005 | Iwasaki et al. | | |

FOREIGN PATENT DOCUMENTS

| | | | |
|---|---|---|---|
| JP | 57-009729 | | 1/1982 |
| JP | 11-246478 | | 9/1999 |
| JP | 2000-119157 | | 4/2000 |
| JP | 2000-312598 | | 11/2000 |
| JP | 2001-199896 | | 7/2001 |
| JP | 2004331651 | * | 7/2003 |
| JP | 2004-331651 | | 11/2004 |
| WO | WO 2004/100942 | * | 11/2004 |
| WO | WO 2005/009682 | | 10/2005 |

OTHER PUBLICATIONS

Macho et al. Non-pungent capsaicinoids from sweet pepper: synthesis and evaluation of the chemopreventive and anticancer potential. Eur J Nutr, 42: pp. 2-9, 2003.*
Translation of JP 2004331651, 2003.*
American Heart Association. Electronic Resource [http://ww.americanheart.org/presenter.jhtml?identifier=4440]. Printer on Jun. 1, 2010.*
Rains et al. Topical Capsaicin: A review of its pharmacological properties and therapeutic potential in post-herpetic neuralgia, diabetic neuropathy and osteoarthritis. (Drugs & Aging, 7(4): 317-328, 1995).*
Valeriani et al. Short-term plastic changes of the human nociceptive system following acute pain induced by capsaicin. Clinical Neurophysiology, 114, 2003, 1879-1890.*
Dihydrocapsaicin. Electronic Resource. Retrieved on Dec. 16, 2010. [http://www.chemblink.com/products/19408-84-5.htm].*
Macho et al. (Eur. J. Nutr. 42: 2-9, 2003).*
Goodman et al. Effect of changing metabolic rate on local blood flow control in the canine hindlimb. Circ. Res. 1978, 43: 769-776.*
Iida, T., et al., "TRPV1 activation and induction of nociceptive response by a non-pungent capsaicin-like compound, capsiate," Neuropharmacology 2003;44:958-967.
Kobata, K., et al., "Novel Capsaicinoid-like Substances, Capsiate and Dihydrocapsiate, from the Fruits of a Nonpungent Cultivar, CH-19 Sweet, of Pepper (*Capsicum annuum* L.)," J. Agric. Food Chem. 1998;46(5):1695-1697.
Kobata, K., et al., "Nordihydrocapsiate, a New Capsinoid from the Fruits of a Nonpungent Pepper, *Capsicum annuum*," J. Nat. Prod. 1999;62:335-336.
Kobata., K., et al., "Enzymatic Synthesis of a Capsinoid by the Acylation of Vanillyl Alcohol with Fatty Acid Derivatives Catalyzed by Lipases," Biosci. Biotechnol. Biochem. 2002;66(2):319-327.
Olmedo, M. V., et al., "Double-blind parallel comparison of multiple doses of ketorolac, ketoprofen and placebo administered orally to patients with postoperative dental pain," Pain 2001;90:135-141.
Watanabe, T., et al., "Effects of Capsaicin Analogs on Adrenal Catecholamine Secretion in Rats," Life Sciences 1994;54(5):369-374.
English Translation of Notification of Reasons for Refusal for Japanese Patent App. No. 2006-024284 (Aug. 30, 2011).

* cited by examiner

*Primary Examiner* — Anna Pagonakis
(74) *Attorney, Agent, or Firm* — Shelly Guest Cermak; Cermak Nakajima & McGowan LLP

(57) ABSTRACT

A topically applied circulation enhancing agent suited for application over the entire body which has good transdermal absorptivity and causes little irritation is provided. A topically applied circulation enhancing agent is provided which contains a fatty acid ester denoted by general formula (1):

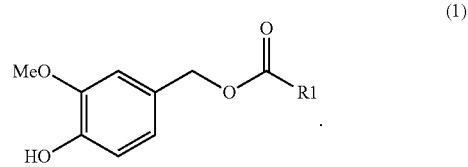

(1)

7 Claims, No Drawings

TOPICALLY APPLIED CIRCULATION ENHANCING AGENT AND SKIN AND HAIR COSMETIC AND BATH AGENT CONTAINING THE SAME

This application claims priority under 35 U.S.C. §119(e) to U.S. provisional application 60/675,895, filed Apr. 29, 2005, and under 35 U.S.C. §119(a) to Japanese patent application 025219/2005, filed Feb. 1, 2005, both of which are incorporated by reference in their entireties.

BACKGROUND OF THE INVENTION

1. Field of the Invention

The present invention relates to topically applied circulation enhancing agents and to skin and hair cosmetics and bath agents containing the same. More specifically, the present invention relates to a topically applied circulation enhancing agent that is suited for use over the entire body, has good solubility, absorbs well through the skin, and causes little irritation; and to skin and hair cosmetics and bath agents containing the same.

2. Brief Description of the Related Art

In recent years, with the widespread use of word processors and personal computers, the number of people assuming a single posture for extended periods of time in the office has increased. This compromises microcirculation and local circulation. There are frequent instances of inadequate blood circulation, resulting in, for example, swollen feet. Seasonal changes also affect life activity. In winter, for example, inadequate peripheral circulation can cause skin problems such as frostbite and chapping. Furthermore, decreased body function with age, anxiety-induced stress, and insomnia also can cause various problems due to inadequate blood circulation.

Swollen feet, puffy eyelids, dark circles around the eye, skin dullness, and the like, that are induced by poor blood circulation are significant problems from the perspective of beauty, and various circulation enhancing agents have been proposed thus far to achieve improvement in this regard.

Examples include a technique (Japanese Patent Application Publication No. 2001-199896) for reducing swelling using a cosmetic containing a fat-degrading agent such as geranii herba extract, and a technique (Japanese Patent Application Publication No. 2000-119157) for reducing swelling with fat-degrading agents such as caffeine, *Houttuynia cordata* extract, and fennel. However, in contrast to the swelling caused by poor blood circulation described above, these techniques are designed to treat swelling caused by the excess accumulation of subcutaneous fat. Furthermore, they are applied only to the face. Still further, since these herbal medicine components have peculiar odors, they are difficult to formulate into cosmetics in effective quantities, which is a drawback.

Capsaicins and their various analogs, such as cayenne pepper powder, cayenne pepper tincture, cayenne pepper extract, capsaicin, homocapsaicin, homodihydrocapsaicin, and vanillyl nonanamide are substances the use of which is known to impart a warm sensation and enhance blood circulation. However, these circulation enhancing agents, typified by capsaicin, are highly irritating and produce an intense, painful burning sensation when applied to the skin, even in small quantities. Although soluble in alcohol, when attempting to dissolve these agents in oils so to mitigate their irritating properties and so they can be blended into various products, these agents have extremely low solubility in the oil bases commonly employed in cosmetics and tend to precipitate as crystals. Thus, they concentrate locally, and it is difficult to achieve a stable circulation enhancing effect by dissolving and diluting them to a concentration suitable for mitigating the irritating sensation they produce. To solve this problem, the synthesis of vanillyl alcohol alkyl ether derivatives (Japanese Patent Application Publication No. Showa 57-9729) such as vanillyl propyl ether, vanillyl butyl ether, vanillyl pentyl ether, and vanillyl hexyl ether has been examined. However, despite an improvement in solubility, the irritating sensation and burning of the skin remain strong. No compound satisfactory for use as a circulation enhancing agent that can be applied over the entire body has yet to be obtained.

As set forth above, although the capsaicins that are the main components of cayenne peppers (capsaicin, dihydrocapsaicin, and the like; hereinafter referred to simply as "capsaicinoids") are well known as having blood circulation enhancing actions and are actually blended into some hot compresses, creams, and the like, the invasiveness and irritating sensation produced on the skin by capsaicins, as well as their low solubility, limit their formulation into cosmetics (Pain (1999), 81 (1, 2), 135-145). Attempts have also been made to improve solubility and reduce irritation by employing vanillyl alcohol alkyl ether derivatives and the like. However, the effects are inadequate and no topically applied circulation enhancing agent that absorbs well through the skin while producing little irritation—nor any skin or hair cosmetic or bath agent containing the same—has been obtained thus far.

SUMMARY OF THE INVENTION

Capsinoid compounds include fatty acid esters of vanillyl alcohols, capsiate (4-hydoxy-3-methoxybenzyl (E)-8-methyl-6-nonenoate), dihydrocapsiate (4-hydroxy-3-methoxybenzyl 8-methylnonanoate), and the like; see Japanese Patent Application Publication No. Heisei 11-246478, and are sometimes referred to hereinafter simply as "capsinoids". These compounds are fatty acid esters which have a variety of physiological activities, do not exhibit spicy flavors, and have been examined for use in orally ingested foods and pharmaceuticals. When the effect of application to the skin was examined, it was surprisingly discovered that these fatty acid esters are highly soluble in various oil bases employed in cosmetics, are absorbed well through the skin, caused almost no irritation or heat sensation when applied to the skin, could be applied to the entire body, and had good blood circulation enhancing effects. The present invention was devised on the basis of this discovery.

That is, the present invention provides a topically applied circulation enhancing agent employing fatty acid esters that is suited to use over the entire body, and skin and hair cosmetics and bath agents containing the same.

It is an object of the present invention to provide a topically applied circulation enhancing agent that has good solubility and transdermal absorptivity, causes little irritation, and is suited for application over the entire body. It is a further object of the present invention to provide skin and hair cosmetics and bath agents containing circulation enhancing agent or blood flow stimulant.

It is an object of the present invention to provide a topically applied circulation enhancing agent comprising a capsinoid compound. That is, it is also an object of the present invention to provide a method of enhancing blood circulation in a subject comprising topically administering an agent comprising a capsinoid compound.

It is a further object of the present invention to provide the topically applied circulation enhancing agent as described above wherein said capsinoid compound comprises the general formula (1):

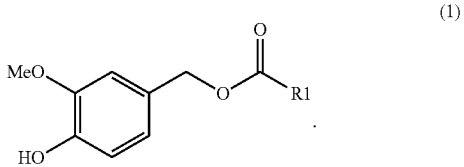

(1)

wherein R1 is selected from the group consisting of an optionally substituted alkyl group having from 5 to 10 carbon atoms and an optionally substituted alkenyl group having from 5 to 10 carbon atoms.

It is still a further object of the present invention to provide the topically applied circulation enhancing agent as described above wherein R1 is selected from the group consisting of hexyl, heptyl, 6-methylheptyl, 5-methylheptyl, octyl, 7-methyloctyl, 6-methyloctyl, trans-7-methyl-5-octnonyl, 8-methylnonyl, 7-methylnonyl, and decyl groups.

It is a further object of the present invention to provide the topically applied circulation enhancing agent as described above wherein said capsinoid compound is selected from the group consisting of capsiate, dihydrocapsiate, nordihydrocapsiate, vanillyl decanoate, vanillyl nonanoate, vanillyl octanoate, vanillyl undecanoate, vanillyl 9-methyl decanoate, vanillyl 6-methyloctanoate, vanillyl 7-methylnonanoate, vanillyl 8-methyldecanoate, and combinations thereof.

It is a further object of the present invention to provide a cosmetic for the skin or hair, or a bath agent, wherein said cosmetic or agent contains the topically applied circulation enhancing agent as described above.

It is a further object of the present invention to provide a compound selected from the group consisting of vanillyl undecanoate, vanillyl 9-methyldecanoate, vanillyl 6-methyloctanoate, vanillyl 7-methylnonanoate, and vanillyl 8-methyldecanoate.

It is a further object of the present invention to provide a method of enhancing blood circulation in a subject comprising topically administering an agent comprising a capsinoid compound as described above.

It is a further object of the present invention to provide the method as described above, wherein the subject is a human.

It is a further object of the present invention to provide the method as described above, wherein said agent is topically administered to the skin or the scalp.

DETAILED DESCRIPTION OF THE PREFERRED EMBODIMENTS

Capsinoids, a type of fatty acid ester, have been discovered in plants belonging to the genus *Capsicum* (Journal of the Horticulture Society 58, 601-607), and confirmed to be edible natural compounds. Despite being structural analogs of capsaicinoids, the capsinoids are not spicy and have been reported to have specific physiological activity, such as immunostimulation activity, energy metabolism activity, and obesity suppressing activity. They are also reported to have no effect when applied to the skin, but this has not been studied in detail (Neuro-pharmacology (2003), 44 (7), 958-967). Accordingly, their effect as topically applied circulation enhancing agents which are absorbed through the skin was discovered for the first time by the present inventors.

The present invention provides a topically applied circulation enhancing agent having good solubility and transdermal absorptivity and causing little irritation that can be applied to the entire body. This agent can be incorporated into skin and hair cosmetics and bath agents to provide cosmetics that cause little irritation and are highly effective in enhancing blood circulation, thereby effectively reducing swollen eyelids, dark rings around the eyes, pale countenance, and the like. This agent can also be incorporated into hair tonics that stimulate hair growth and development. This agent can also be incorporated into bath agents that are highly effective at helping people recover from fatigue by enhancing blood circulation throughout the body.

The topically applied circulation enhancing agent of the present invention can be used to provide skin and hair cosmetics and bath agents that effectively reduce swollen feet, puffy eyelids, dark rings around the eyes, pale countenance, and the like induced by poor circulation. Specific examples of the present invention are described below.

The capsinoid compound employed as an active ingredient in the topically applied circulation enhancing agent of the present invention is a vanillyl alcohol fatty acid ester. Representative compounds are components confirmed to be present in cayenne peppers, such as capsiate, dihydrocapsiate, nordihydrocapsiate, as well as various fatty acid esters including straight-chain fatty acids and vanillyl alcohol such as vanillyl decanoate (4-hydroxy-3-methoxybenzyl decanoate (caprate)), vanillyl nonanoate (4-hydroxy-3-methyloxybenzyl nonanoate), and vanillyl octanoate (4-hycroxy-3-methoxybenzyl octanoate).

Accordingly, the capsinoid compound can be denoted by general formula (1) below:

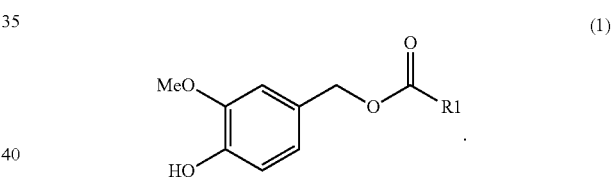

(1)

wherein R1 denotes an optionally substituted alkyl group having from 5 to 10 carbon atoms or an optionally substituted alkenyl group having from 5 to 10 carbon atoms. In a possible optional aspect of the invention, the genus of general formula (1) does not include vanillyl nonanoate.

Examples of the alkyl group having from 5 to 10 carbon atoms, which may be a straight or branched chain, include n-pentyl, sec-pentyl, tert-pentyl, isopentyl, n-hexyl, isohexyl, heptyl, octyl, nonyl, decyl, and undecyl groups. Various branched chain isomers of these groups are also included. Branched chain is preferred as those are confirmed to exist in natural peppers.

Examples of the alkenyl group having from 5 to 10 carbon atoms, which may be a straight or branched chain and may have one or more double bonds, include pentenyl, hexenyl, heptenyl, octenyl, nonenyl, decenyl, and undecenyl groups. Further examples are branched chain isomers of these groups. The position of the double bonds may be either trans or cis; the trans form is preferred.

These groups may also be optionally substituted with 1-4 substituents. Examples of these substituents are halogen atoms and alkyl, haloalkyl, amino, hydroxyl, acyl, nitro, cyano, and thiol groups. Of these, substitution with a short-chain alkyl group having 1 to 4 carbon atoms is desirable. Examples of alkyl groups having from 1 to 4 carbon atoms are methyl, ethyl, propyl, isopropyl, butyl, t-butyl, and isobutyl groups. Of these substituents, methyl and ethyl groups are preferred, with the hydrogen atoms on the second or third carbon atom from the end on the methyl side desirably being substituted.

R1 desirably denotes a hexyl, heptyl, 6-methylheptyl, 5-methylheptyl, octyl, 7-methyloctyl, 6-methyloctyl, trans-7-methyl-5-octyenyl, nonyl, 8-methylnonyl, 7-methylnonyl, or decyl group.

Of these, in the new compounds initially synthesized in the form of vanillyl undecanoate, vanillyl 9-methyldecanoate, vanillyl 6-methyloctanoate, vanillyl 7-methylnonanoate, and vanillyl 8-methyldecanoate, R1 denotes a decyl, 8-methylnonyl, 5-methylheptyl, 6-methyloctyl, and 7-methylnonyl group, respectively. Accordingly, the present invention also covers inventions relating to these compounds.

Of these, capsiate, dihydrocapsiate, and nordihydrocapsiate are preferred examples because they are present in large quantities in non-spicy cayenne pepper. These compounds have the following structural formulas:

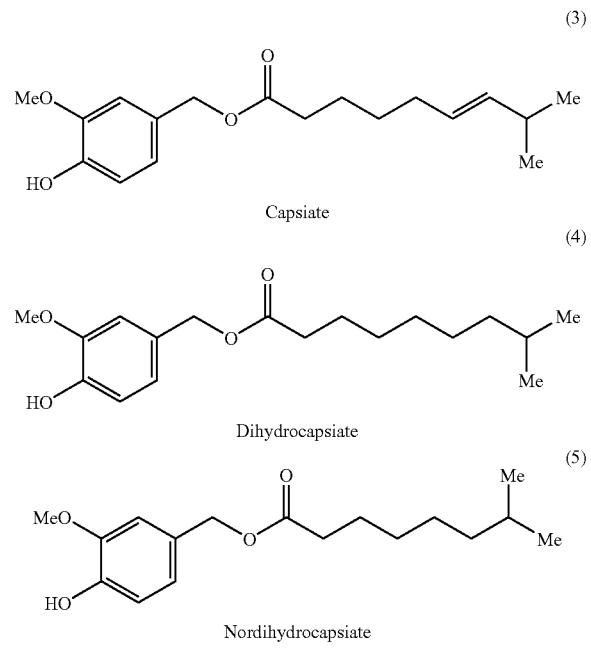

Furthermore, vanillyl decanoate, vanillyl nonanoate, vanillyl octanoate, vanillyl undecanoate, vanillyl 9-methyldecanoate, vanillyl 6-methyloctanoate, vanillyl 7-methylnonanoate, and vanillyl 8-methyldecanoate are desirable because they have about the same degree of activity as capsiate.

Since the above-described capsinoid compounds are contained in large quantities in plants of the genus *Capsicum*, they can be prepared by extraction, separation, and purification from the body and/or fruit of plants of the genus *Capsicum* (referred to as "peppers" hereinafter). The pepper used for extraction may be derived from a variety of peppers having the usual spicy flavor, typified by the "Nikko" and "Goshiki" varieties. However, peppers containing intensely stimulating capsaicins are undesirable. Thus, the use of common non-spicy varieties of pepper containing large amounts of capsinoids, such as "CH-19 Sweet," "Manganji," "Fushimiamanaga," green peppers, and bell peppers is desirable. Here, the term "CH-19 Sweet" covers both the "CH-19 Sweet" variety and subsequent analog varieties derived from it. In the present Description, the term "CH-19 Sweet" covers all of these. Extraction, separation, and purification may be conducted by means well known to those skilled in the art, such as solvent extraction and various forms of chromatography such as silica gel chromatography and preparation-use high performance liquid chromatography, either singly or in suitable combination. For example, the method described in Japanese Patent Application Publication No. Heisei 11-246478 may be employed.

For example, the above-described capsinoid compounds can be synthesized by transesterification employing the corresponding fatty acid ester and vanillyl alcohol as starting materials according to the description given in Japanese Patent Application Publication No. Heisei 11-246478. Alternatively, based on the structural formula, synthesis may be conducted by other reaction methods known to those skilled in the art. Still further, capsinoid compounds can be readily prepared by synthesis methods employing enzymes. For example, the method described in Japanese Patent Application Publication No. 2000-312598 may be employed to obtain a desired fatty acid ester using a lipase reverse reaction employing an ester of the fatty acid corresponding to the desired compound and/or a compound such as a triglyceride having that fatty acid and vanillyl alcohol as substrate.

In the structure of capsinoids, the amide bond of capsaicin is changed to an ester bond, thereby imparting a variety of properties differing from those of capsaicin. That is, when administered to the human body either orally or transdermally, capsinoids produce a much less spicy taste and cause much less irritation than capsaicins, and have greatly improved solubility in various organic solvents. As a result, they improve application on the skin when using an organic solvent medium, and enhance transdermal absorption. When employed as topically applied circulation enhancing agents in skin and hair cosmetics, bath agents, and the like, capsinoids are characterized by ease of formulation design and blending, a pleasant sensation when used, and particularly effective enhancement of blood circulation.

Conventionally employed circulation enhancing agents may also be suitably incorporated into the circulation enhancing agent of the present invention. Examples of such conventional circulation enhancing agents are cayenne pepper powder, cayenne pepper tincture, cayenne pepper extract, capsaicin, homocapsaicin, homodihydrocapsaicin, vanillyl nonanamide, capsaicin, ginger extract, cayenne pepper extract, nicotinic acid, *Sophorae Radix* extract, *Astragali Radix* extract, *Zingiberis Siccatum Rhizoma* extract, *Carthami Flos* extract, *Zanthoxylum piperitum* extract, *Salvia militiorhhiza* extract, *Panacis Japonici Rhizoma* extract, Korean ginseng extract, and γ-aminobutyric acid (GABA).

Furthermore, various components commonly employed in cosmetics and topically applied skin agents may be added to the circulation enhancing agent of the present invention within a content range that does not compromise the effect of the present invention. Examples of such components are oil bases, surfactants, polymeric substances, solvents, powders, antioxidants, antiinflammatory agents, ultraviolet-absorbing agents, whitening agents, cell growth ingredients, moisturizing agents, metal chelate pigments, fragrances, and transdermal absorption enhancing agents.

Examples of oil bases are squalane, liquid paraffin, light liquid isoparaffin, heavy liquid isoparaffin, microcrystalline waxes, solid paraffin, and other hydrocarbons; dimethicone, phemethicone, cyclomethicone, ammodimethicone, polyether-modified silicone, and other silicones; jojoba oil, carnauba wax, Japan wax, beeswax, spermaceti, octyldodecyl oleate, isopropyl myristate, neopentyl glycol diisostearate, malic acid diisostearate, and other esters; stearic acid, lauric acid, myristic acid, palmitic acid, isostearic acid, isopalmitic acid, behenic acid, oleic acid, and other fatty acids; acyl glutamic acid, acyl glycine, acyl alanine, acyl sarcosine, and other acyl amino acids; behenyl alcohol, cetanol, oleyl alcohol, octadecyl alcohol, and other higher alcohols; castor oil, coconut oil, hydrogenated castor oil, *Cedrela sinensio* oil, wheat germ oil, isostearic acid triglyceride, isooctanoic acid triglyceride, olive oil, and other triglycerides.

Examples of surfactants are sorbitan sesquioleate, sorbitan monooleate, sorbitan trioleate, sorbitan sesquistearate, sorbitan monostearate, polyoxyethylene sorbitan monooleate, polyoxyethylene sorbitan monostearate, polyoxyethylene stearate, polyoxyethylene oleate, polyoxyethylene glyceryl fatty acid ester, polyoxyethylene alkyl ether, polyoxyethylene hardened castor oil, and other nonionic surfactants; sodium lauryl stearate, polyoxyethylene alkyl sulfate, sulfosuccinic acid ester salt, acyl glutamic acid salt, acyl sarcosine salt, acyl glycine salt, acryl alanine salt, and other anionic surfactants; quaternary alkyl ammonium salts and other cationic surfactants; alkyl betaine and other amphoteric surfactants; emulsifiers; and solubilizing agents.

Examples of solvents are ethanol and other lower alcohols; 1,2-pentanediol, 1,2-hexyleneglycol, isoprene glycol, and other polyhydric alcohols; ethers; other organic solvents; and water.

Examples of polymeric substances are polyaspartic acid, $\epsilon$-polylysine, $\gamma$-polyglutamic acid, and other polyamino acids and their derivatives; collagen, elastin, and other natural polymeric compounds; partially deacetylated chitin and other semisynthetic polymer compounds; and carboxymethyl cellulose and other synthetic polymer compounds.

Examples of powders are crystalline cellulose, crosslinked methyl polysiloxane, polyethylene powder, acrylic resin powder, and other organic powders; talc, mica, sericite, magnesium carbonate, calcium carbonate, titanium dioxide, iron oxide, Berlin blue pigment, ultramarine pigment, titanium mica, titanium sericite, silica, and other optionally surface-treated powders; microparticulate compound powders (hybrid fine powders), titanium dioxide-coated mica, and other nacreous pigments; photochromic pigments; nylon powders and other polymer powders; N-$\epsilon$-lauroyllysine; and other organic powders.

Examples of pigments are legal tar pigment type 1, legal tar pigment type 2, legal tar pigment type 3, wool dyes, natural pigments, and mineral pigments.

Examples of fragrances are animal fragrances such as musks; vegetable fragrances such as jasmine oil; synthetic fragrances such as $\alpha$-amylcinnamaldehyde; and mixed fragrances.

Examples of transdermal absorption enhancing agents are urea, 2-pyrrolidone, 1-hexanol, 1-octanol, 1-decanol, 1-menthol, sodium lauryl sulfate, isopropyl myristate, n-hexyl acetate, and oleic acid.

As needed, various other components from among those set forth above can be blended into the topically applied circulation enhancing agent of the present invention by the usual methods to obtain skin and hair cosmetics, bath agents, and toiletry products. The formulation is not specifically limited; these products may be in the form of solutions, pastes, gels, solids, powders, or any other formulation. Examples are oils, lotions, creams, emulsions, gels, shampoos, hair rinses, hair conditioners, enamels, foundations, lipsticks, toilet powders, packs, ointments, granules, capsules, perfumes, powders, eaux de cologne, toothpastes, soaps, aerosols, and cleansing creams. Furthermore, the topically applied circulation enhancing agent of the present invention may be employed in hair tonics, anti-aging and enhancing agents for the skin, essence, agents for preventing and treating rough skin caused by chapping and cracking, and other pharmaceutical and nonpharmaceutical products employed to prevent and treat various skin ailments.

EXAMPLES

The present invention will be described in greater detail through the following non-limiting examples. However, the present invention is not limited to these examples. In the examples, blending quantities are given as weight percentages.

Example 1

The solubility of capsinoids (a mixed product prepared by the method stated in Reference Example (5) was employed; see below) and capsaicin was compared in various oils at room temperature. As will be clear from Table 1, capsaicin did not dissolve in the various cosmetic oils and crystal precipitation was observed. By contrast, the capsinoids, which were originally liquid at room temperature, were confirmed to rapidly and uniformly dissolve into the various oils when simply added in a prescribed quantity. Based on this result, it was found that when blended into creams, emulsions, and other cosmetic products, the capsinoids were more uniformly and readily emulsified and dispersed and better facilitated concentration adjustment and manufacturing than did capsaicin.

TABLE 1

| | Capsinoids | | Capsaicin | |
|---|---|---|---|---|
| Oil | 1 wt % | 5 wt % | 1 wt % | 5 wt % |
| Olive oil | ○ | ○ | X | X |
| *Cedrela sinensio* oil | ○ | ○ | X | X |
| Castor oil | ○ | ○ | X | X |
| Liquid paraffin | ○ | ○ | X | X |
| Squalane | ○ | ○ | X | X |
| Isopropyl myristate | ○ | ○ | X | X |

(○: uniform dissolution; X: precipitation of crystals)

Example 2

The vasodilating effects of capsinoids (a mixed product prepared by the method stated in Reference Example (5) was employed; see below) and capsaicin was compared using the conchae of hairless mice.

Test Method: A sample was applied on the right ear and a control was applied on the left ear of a hairless mouse (HR-1, female), and the development of red spots was visually evaluated.

Sample: (1) Capsinoids (1 weight percent and 5 weight percent dissolved in liquid paraffin)

(2) Capsaicin (1 weight percent and 5 weight percent dispersed in liquid paraffin)

Control: Liquid paraffin

Results of visual evaluation: At 1 weight percent, red spots were observed for capsaicin but not for the capsinoids. At 5 weight percent, 30 minutes after application, clear red spots were observed on the conchae for both capsaicin and capsinoids. The red spots that developed disappeared completely after about two hours for the capsinoids, but even at the 1 weight percent application, the red spots caused by capsaicin retained their original form even after two hours. For the liquid paraffin application of the control, no red spots were observed. As will be seen from the results of Example 1, capsaicin did not fully dissolve into liquid paraffin, but was evaluated in a dispersed state for both 1 and 5 weight percent.

From these results, it was determined that while capsaicin had a strong circulation enhancing action and prolonged duration, the capsinoids had suitable duration and intensity, and constituted a desirable circulation enhancing agent for use in cosmetics.

Example 3

The vasodilating effect and irritating sensation of capsinoids (a mixed product prepared by the method stated in Reference Example (5) was employed; identical below) were evaluated on human cheeks.

Test Method:
Application site: the cheeks (on either side of the nose)
Sample: 30 weight percent of capsinoid (in isopropyl alcohol)
Control: Isopropyl alcohol
Volunteers: 5 men
Test procedure: As follows. The samples were prepared in double blind fashion and the applying sequence and site (either right or left cheek) were random.
(1) Before evaluation, the oil on the applied site was removed with ethanol.
(2) Sample was applied to the right (or left) cheek (using a cotton swab).
(3) The control was applied on the opposite cheek from (2) (using a cotton swab).
(4) The following was evaluated:
(a) A determination was made by the evaluator by visually comparing the level of red spotting to the control site.
(b) The subject compared the irritating sensation to that of the control site.
Results: Both an irritating sensation and red spotting were confirmed for the sites where the sample was applied.
As regards the irritating sensation:

| | |
|---|---|
| No irritating sensation but some feeling of discomfort | 3 people |
| A slight irritating sensation was experienced | 1 person |
| An irritating sensation was experienced | 1 person |

As regards red spotting:

| | |
|---|---|
| Some red spotting was observed | 3 people |
| Clear red spotting was observed | 2 people |

Despite the application of a high concentration of 30 weight percent, more than half of the people experienced only a slightly irritating sensation or a sensation of discomfort, and the sensation disappeared within two hours. Some effect on red spotting was observed in nearly all of the subjects; tests on the human face revealed that capsinoid enhanced blood circulation without producing irritation.

Example 4

In the same manner as in Example 2, the vasodilating effects of various capsinoid compounds were compared using the conchae of hairless mice. The samples were dissolved in liquid paraffin.
Sample: (1) Vanillyl alcohol (5 weight percent dispersed in liquid paraffin)
(2) Capsaicin (1 and 5 weight percent dispersed in liquid paraffin)
(3) Capsiate (1 and 5 weight percent dissolved in liquid paraffin)
(4) Dihydrocapsiate (1 and 5 weight percent dissolved in liquid paraffin)
(5) Nordihydrocapsiate (1 and 5 weight percent dissolved in liquid paraffin)
(6) Vanillyl octanoate (1 and 5 weight percent dissolved in liquid paraffin)
(7) Vanillyl decanoate (1 and 5 weight percent dissolved in liquid paraffin)
(8) Vanillyl undecanoate (1 and 5 weight percent dissolved in liquid paraffin)
(9) Vanillyl dodecanoate (1 and 5 weight percent dissolved in liquid paraffin)
(10) Vanillyl tridecanoate (1 and 5 weight percent dissolved in liquid paraffin)
(11) Vanillyl pentadecanoate (1 and 5 weight percent dissolved in liquid paraffin)
(12) Vanillyl octadecanoate (1 and 5 weight percent dissolved in liquid paraffin)
(13) Vanillyl oleate (1 and 5 weight percent dissolved in liquid paraffin)
(14) Vanillyl linolenate (1 and 5 weight percent dissolved in liquid paraffin)
(15) Vanillyl 9-methyldecanoate (1 and 5 weight percent dissolved in liquid paraffin)
(16) Vanillyl 6-methyloctanoate (1 and 5 weight percent dissolved in liquid paraffin)
(17) Vanillyl 7-methylnonanoate (1 and 5 weight percent dissolved in liquid paraffin)
(18) Vanillyl 8-methyldecanoate (1 and 5 weight percent dissolved in liquid paraffin)
Control: Liquid Paraffin The results are given in Table 2. Based on these results, capsinoid compounds having side-chain fatty acids with 11 or fewer carbon atoms were observed to have blood circulation promoting effects when topically administered. Both mixtures of capsinoid compounds and single components were found to exhibit equivalent effects. Of these, the compounds newly synthesized by the present inventors—vanillyl undecanoate, vanillyl 9-methyldecanoate, vanillyl 6-methyloctanoate, vanillyl 7-methylnonanoate, vanillyl 8-methyldecanoate—were observed to have similar activity.

TABLE 2

| Sample | 5 wt % | 1 wt % | Remarks |
|---|---|---|---|
| Vanillyl alcohol | X | — | No vasodilating effect |
| Capsaicin | ◯ | ◯ | 1 weight percent application, the red spots caused even after two hours |
| Capsiate | ◯ | Δ | 5 weight percent application, the weak red spots caused even after 90 minutes |

TABLE 2-continued

| Sample | 5 wt % | 1 wt % | Remarks |
|---|---|---|---|
| Dihydrocapsiate | ○ | Δ | 5 weight percent application, the weak red spots caused even after 90 minutes |
| Nordihydrocapsiate | ○ | Δ | 5 weight percent application, the weak red spots caused even after 90 minutes |
| Vanillyl octanoate (C8) | ○ | X | Vasodilating effect disappeared in about one hour |
| Vanillyl decanoate (C10) | ○ | X | Vasodilating effect disappeared in about one hour |
| Vanillyl undecanoate (C11) | ○ | X | Had a weaker vasodilating effect than C10, and the effect disappeared more quickly than for C10. |
| Vanillyl dodecanoate (C12) | X | — | No vasodilating effect |
| Vanillyl tridecanoate (C15) | X | — | No vasodilating effect |
| Vanillyl pentadecanoate (C15) | — | — | Not dissolved |
| Vanillyl octadecanoate (C18) | X | — | No vasodilating effect |
| Vanillyl oleate | X | — | No vasodilating effect |
| Vanillyl linolenate | X | — | No vasodilating effect |
| Vanillyl 9-methyldecanoate | ○ | X | 5 weight percent application, vasodilating effect disappeared in about two hour |
| Vanillyl 6-methyloctanoate | ○ | X | 5 weight percent application, vasodilating effect disappeared in about two hour |
| Vanillyl 7-methylnonanoate | ○ | X | 5 weight percent application, vasodilating effect disappeared in about two hour |
| Vanillyl 8-methyldecanoate | ○ | X | 5 weight percent application, vasodilating effect disappeared in about two hour |

Formulation Example 1

Cream

| | |
|---|---|
| Capsiate | 1.0 wt % |
| Stearic acid | 2.0 |
| Polyoxyethylene (25) cetyl ether | 3.0 |
| Glyceryl monostearate | 2.0 |
| Octyl dodecanol | 10.0 |
| Cetanol | 6.0 |
| Hydrogenated lanolin | 4.0 |
| Squalane | 9.0 |
| 1,3-Butylene glycol | 6.0 |
| Polyethylene glycol (1500) | 4.0 |
| Preservative | suitable quantity |
| Fragrance materials | suitable quantity |
| Antioxidant | suitable quantity |
| Purified water | suitable quantity |

Formulation Example 2

Emulsion

| | |
|---|---|
| Capsiate | 2.0 wt % |
| Sorbitan sesquioleate | 2.0 |
| Polyoxyethylene oleoyl ether | 2.5 |
| Stearyl alcohol | 0.5 |
| Hydrogenated palm oil | 3.0 |
| Liquid paraffin | 35.0 |
| Dipropylene glycol | 6.0 |
| Polyethylene glycol (400) | 4.0 |
| Carboxyvinyl polymer (1 percent aqueous solution) | 15.0 |
| Preservative | suitable quantity |
| Fragrance materials | suitable quantity |
| Purified water | remainder |

Formulation Example 3

Gel

| | |
|---|---|
| Capsiate | 0.5 wt % |
| Liquid paraffin | 12.0 |
| Tri(2-ethyl hexanoic acid)glyceryl | 50.0 |
| Sorbitol | 10.0 |
| Polyethylene glycol (400) | 5.0 |
| Acyl methyl taurine | 5.0 |
| Polyoxyethylene (20) isocetyl ether | 10.0 |
| Fragrance materials | suitable quantity |
| Preservative | suitable quantity |
| Purified water | remainder |

Formulation Example 4

Beauty Rinse

| | |
|---|---|
| Dihydrocapsiate | 1.0 wt % |
| p-Methoxycinnamic acid-2-ethylhexyl | 4.0 |
| 3,3'-(1,4-phenylenedimethylidene)bis(7,7-dimethyl-2-oxo-bicyclo(2,2,1)heptane-1-methanesulfonic acid) | 4.0 |
| Polyoxyethylene cetyl ether | 2.0 |
| Glycerin monostearate | 2.0 |
| Stearic acid | 3.0 |
| Cetanol | 1.0 |
| Lanolin | 3.0 |
| Liquid paraffin | 5.0 |
| 2-Ethylhexyl stearate | 3.0 |
| 1,3-Butylene glycol | 6.0 |
| Fragrance materials | suitable quantity |
| Preservative | suitable quantity |
| Purified water | remainder |

Formulation Example 5

Eau de Toilette

| | |
|---|---|
| Capsiate | 3.0 wt % |
| Glycerin | 3.0 |
| Sorbitol | 2.0 |
| Polyoxyethylene (20) oleyl ether | 1.0 |
| Ethanol | 15.0 |
| Zinc p-phenolsulfonate | 0.2 |
| Fragrance materials | suitable quantity |
| Preservative | suitable quantity |
| Purified water | remainder |

Formulation Example 6

Hair Tonic

| | |
|---|---|
| Capsiate | 2.0 wt % |
| Swertia japonica extract | 0.1 |
| Hyaluronic acid | 0.2 |
| Hinokitiol | 0.2 |
| Vitamin B6 | 0.5 |
| Vitamin E | 0.5 |
| Urea | 2.5 |
| Polyproylene glycol | 4.0 |
| Ethanol | 50.0 |
| Fragrance materials | suitable quantity |
| Preservative | suitable quantity |
| Purified water | remainder |

Formulation Example 7

Jelly Peel-Off Pack

| | |
|---|---|
| Capsiate | 2.0 wt % |
| Jojoba oil | 1.0 |
| Squalane | 1.0 |
| PEG400 | 5.0 |
| Sorbitol | 5.0 |
| Ethanol | 8.0 |
| Polyvinyl alcohol | 10.0 |
| Polyvinyl acetate emulsion | 15.0 |
| Titanium oxide | 5.0 |
| Talc | 10.0 |
| POE sorbitan monostearic acid ester | 1.0 |
| Fragrance materials | suitable quantity |
| Preservative | suitable quantity |
| Purified water | remainder |

Formulation Example 8

Milk Bath

| | |
|---|---|
| Capsiate | 5.0 wt % |
| Liquid paraffin | 55.0 |
| Squalane | 10.0 |
| Macadamia nut oil | 10.0 |
| Sorbitan oleate | 10.0 |
| POE oleyl ether | 10.0 |
| Fragrance materials | suitable quantity |
| Preservative | suitable quantity |

REFERENCE EXAMPLES

Synthesis of Capsinoids

The capsinoids employed in the tests were synthesized using fatty acid methyl esters or fatty acids based on the method described in Kobata et al. (*Biosci. Biotechnol. Biochem.*, 66(2), 319-327, 2002) below or an improved version thereof. Representative examples are described below.

(1) Synthesis of Vanillyl Decanoate

This compound was synthesized by the method described in Kobata et al. (*Biosci. Biotechnol. Biochem.*, 66(2), 319-327, 2002). Decanoic acid methyl ester (2.13 mL, 10.5 mmol), vanillyl alcohol (1.62 g, 10.5 mmol), molecular sheaves 4 Å (10 g), and Novozyme 435 (2.5 g) were added to acetone (50 mL) and stirred for 2 hours at room temperature. The reaction solution was filtered through cellite and the filtrate was concentrated under reduced pressure. The concentrated residue was purified by silica gel chromatography, yielding 2.25 g (7.30 mmol, 73.0 percent) of vanillyl decanoate in the form of a colorless oily substance.

$^1$H-NMR (CDCl3, δ): 0.87 (t, 3H, J=7.1 Hz), 1.18-1.30 (m, 12H), 1.55-1.65 (m, 2H), 2.33 (t, 2H, J=7.7 Hz), 3.90 (s, 3H), 5.03 (s, 2H), 5.64 (br, 1H), 6.80-6.90 (m, 3H).

(2) Synthesis of Capsiate

Using trans-8-methyl-6-noneic acid methyl ester synthesized by the method described in Kaga et al. (*Tetrahedron*, 52(25), 8451-8470, 1996), capsiate was synthesized by the method described in Kobata et al. (*Biosci. Biotechnol. Biochem.*, 66(2), 319-327, 2002).

$^1$H-NMR (CDCl3, δ): 0.95 (d, 6H, J=6.74 Hz), 1.33-1.40 (m, 2H), 1.59-1.67 (m, 2H), 1.94-1.99 (m, 2H), 2.18-2.23 (m, 1H), 2.33 (t, 2H, J=7.52 Hz), 3.89 (s, 3H) 5.02 (s, 2H), 5.26-5.39 (m, 2H), 5.63 (br, 1H), 6.83-6.90 (m, 3H).

(3) Synthesis of Dihydrocapsiate

Commercial 8-methylnonanoic acid was converted to methyl ester and used to synthesize dihydrocapsiate by the method described in Kobata et al. (*Biosci. Biotechnol. Biochem.*, 66(2), 319-327, 2002).

$^1$H-NMR (CDCl3, δ): 0.86 (d, 6H, J=6.60 Hz), 1.12-1.37 (m, 8H), 1.46-1.64 (m, 3H), 2.32 (t, 2H, J=7.56 Hz), 3.89 (s, 3H), 5.02 (s, 2H), 5.63 (br, 1H), 6.83-6.90 (m, 3H).

(4) Synthesis of Nordihydrocapsiate

This compound was prepared by the method described in Kobata et al. (*Biosci. Biotechnol. Biochem.*, 66(2), 319-327, 2002), using commercial 7-methyloctanoic acid methyl ester.

$^1$H-NMR (CDCl3, δ): 0.86 (d, 6H, J=5.64 Hz), 1.10-1.16 (m, 2H), 1.22-1.32 (m, 4H) 1.42-1.68 (m, 3H), 2.33 (t, 2H, J=7.68 Hz), 3.90 (s, 3H), 5.02 (s, 2H), 5.63 (s, 1H), 6.83-6.90 (m, 3H).

(5) Synthesis of a Mixture of Three Capsinoids

The triple capsinoids mixture employed in the present invention was enzymatically synthesized using starting materials in the form of a mixture of three fatty acid methyl esters obtained by circulating capsaicin in methanolic hydrate chloric acid and vanillyl alcohol. Specifically, the molar ratio of fatty acid methyl esters to vanillyl alcohol was 1:5. The enzyme employed was immobilized lipase (product name: Novozyme 435, made by Novozyme Corp.). The synthesis reaction was conducted at 25° C. for 45 hours. The yield was 71.7 percent. The purity was 97.5 percent based on capsinoid. The content ratio of capsiate, dihydrocapsiate, and nordihydrocapsiate was 62:30:7 as analyzed by HPLC.

(6) Synthesis of Vanillyl Octanoate

This compound was prepared by the method described in Kobata et al. (*Biosci. Biotechnol. Biochem.*, 66(2), 319-327, 2002), using commercial octanoic acid.

$^1$H-NMR (CDCl3, δ): 0.88 (d, 3H, J=7.10 Hz), 1.20-1.35 (m, 8H), 1.60-1.70 (m, 2H), 2.35 (t, 2H, J=7.40 Hz), 3.90 (s, 3H), 5.03 (s, 2H), 6.83-6.90 (m, 3H).

(7) Synthesis of Vanillyl Undecanoate

This compound was prepared by the method described in Kobata et al. (*Biosci. Biotechnol. Biochem.*, 66(2), 319-327, 2002), using commercial undecanoic acid.

$^1$H-NMR (CDCl3, δ): 0.88 (d, 3H, J=6.76 Hz), 1.20-1.35 (m, 14H), 1.58-1.68 (m, 2H) 2.35 (t, 2H, J=7.68 Hz), 3.90 (s, 3H), 5.03 (s, 2H), 6.83-6.90 (m, 3H).

(8) Synthesis of Vanillyl 9-methyldecanoate

An improved form of the method of Hassarajani et al. (*J. Chem. Research(S)*, 219, 1993) was employed to synthesize 9-methyldecanoic acid, after which the above compound was synthesized by the method described in Kobata et al. (*Biosci. Biotechnol. Biochem.*, 66(2), 319-327, 2002).

$^1$H-NMR (CDCl3, δ): 0.86 (d, 6H, J=6.64 Hz), 1.12-1.35 (m, 10H), 1.45-1.55 (m, 1H) 1.50-1.60 (m, 2H), 2.34 (t, 2H, J=7.44 Hz), 3.89 (s, 3H), 5.03 (s, 2H), 6.83-6.90 (m, 3H)

(9) Synthesis of Vanillyl 6-methyloctanoate

An improved form of the method of Hassarajani et al. (*J. Chem. Research(S)*, 219, 1993) was employed to synthesize 6-methyloctanoic acid, after which the above compound was synthesized by the method described in Kobata et al. (*Biosci. Biotechnol Biochem.*, 66(2), 319-327, 2002).

$^1$H-NMR (CDCl3, δ): 0.80-0.90 (m, 6H), 1.05-1.19 (m, 2H), 1.22-1.40 (m, 5H), 1.60-1.70 (m, 2H), 2.34 (t, 2H, J=7.56 Hz), 3.89 (s, 3H), 5.03 (s, 2H), 6.85-6.91 (m, 3H).

(10) Synthesis of Vanillyl 7-methylnonanoate

An improved form of the method of Hassarajani et al. (*J. Chem. Research(S)*, 219, 1993) was employed to synthesize 7-methylnonanoic acid, after which the above compound was synthesized by the method described in Kobata et al. (*Biosci. Biotechnol. Biochem.*, 66(2), 319-327, 2002).

$^1$H-NMR (CDCl3, δ): 0.80-0.90 (m, 6H), 1.05-1.20 (m, 2H), 1.20-1.38 (m, 7H), 1.60-1.70 (m, 2H), 2.34 (t, 2H, J=7.72 Hz), 3.90 (s, 3H), 5.03 (s, 2H), 6.85-6.91 (m, 3H).

(11) Synthesis of Vanillyl 8-methyldecanoate

An improved form of the method of Hassarajani et al. (*J. Chem. Research(S)*, 219, 1993) was employed to synthesize 8-methyldecanoic acid, after which the above compound was synthesized by the method described in Kobata et al. (*Biosci. Biotechnol. Biochem.*, 66(2), 319-327, 2002).

$^1$H-NMR (CDCl3, δ): 0.80-0.90 (m, 6H), 1.02-1.20 (m, 2H), 1.20-1.40 (m, 9H), 1.60-1.70 (m, 2H), 2.34 (t, 2H, J=7.72 Hz), 3.90 (s, 3H), 5.03 (s, 2H) 6.85-6.91 (m, 3H).

(12) Synthesis of Vanillyl n-tridecanoate, n-pentadecanoate, stearate, oleate, and linolate These compounds were prepared by the method described in Kobata et al. (Biosci. Biotechnol. Biochem., 66(2), 319-327, 2002), using commercial n-tridecanoic acid, n-pentadecanoic acid, stearic acid, oleic acid, and linoleic acid.

While the invention has been described in detail with reference to the preferred embodiments thereof, it will be apparent to one of skill in the art that various changes can be made, and equivalents employed, without departing from the scope of the invention. Each of the aforementioned documents is incorporated by reference herein in its entirety.

We claim:

1. A method of enhancing blood circulation in a subject in need of enhanced blood circulation comprising topically administering an agent comprising a capsinoid compound, wherein the concentration of said capsinoid compound in said agent is from 0.5 weight % to 5.0 weight %.

2. The method of claim 1, wherein said capsinoid compound comprises the general formula (1):

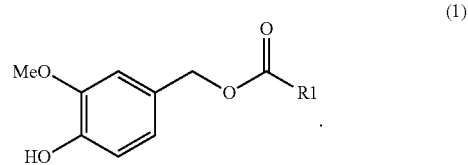

wherein R1 is selected from the group consisting of an optionally substituted alkyl group having from 5 to 10 carbon atoms and an optionally substituted alkenyl group having from 5 to 10 carbon atoms.

3. The method of claim 2, wherein R1 is selected from the group consisting of hexyl, heptyl, 6-methylheptyl, 5-methylheptyl, octyl, 7-methyloctyl, 6-methyloctyl, trans-7-methyl-5-octenyl, nonyl, 8-methylnonyl, 7-methylnonyl, and decyl.

4. The method of claim 1, wherein said capsinoid compound is selected from the group consisting of capsiate, dihydrocapsiate, nordihydrocapsiate, vanillyl decanoate, vanillyl nonanoate, vanillyl octanoate, vanillyl undecanoate, vanillyl 9-methyldecanoate, vanillyl 6-methyloctanoate, vanillyl 7-methylnonanoate, and vanillyl 8-methyldecanoate.

5. The method of claim 1, wherein said subject is human.

6. The method of claim 1, wherein said agent is topically administered to the skin.

7. The method of claim 1, wherein said agent is topically administered to the scalp.

* * * * *